United States Patent
Tian et al.

(10) Patent No.: US 11,324,455 B2
(45) Date of Patent: May 10, 2022

(54) ARTIFICIAL INTELLIGENCE-BASED INTERFERENCE RECOGNITION METHOD FOR ELECTROCARDIOGRAM

(71) Applicant: Shanghai Lepu CloudMed Co., Ltd, Shanghai (CN)

(72) Inventors: Liang Tian, Changping District Beijing (CN); Xue Zhang, Changping District Beijing (CN); Yue Zhang, Changping District Beijing (CN); Zifang Zhao, Changping District Beijing (CN); Zhiqiang Su, Changping District Beijing (CN); Jun Cao, Changping District Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 175 days.

(21) Appl. No.: 16/615,690

(22) PCT Filed: Jan. 12, 2018

(86) PCT No.: PCT/CN2018/072349
§ 371 (c)(1),
(2) Date: Nov. 21, 2019

(87) PCT Pub. No.: WO2019/100561
PCT Pub. Date: May 31, 2019

(65) Prior Publication Data
US 2020/0121255 A1 Apr. 23, 2020

(30) Foreign Application Priority Data
Nov. 27, 2017 (CN) .......................... 201711203069.4

(51) Int. Cl.
*A61B 5/00* (2006.01)
*A61B 5/0428* (2006.01)
(Continued)

(52) U.S. Cl.
CPC ............ *A61B 5/7221* (2013.01); *A61B 5/303* (2021.01); *A61B 5/352* (2021.01); *A61B 5/366* (2021.01); *A61B 5/7267* (2013.01)

(58) Field of Classification Search
CPC ....... A61B 5/7221; A61B 5/303; A61B 5/352; A61B 5/366; A61B 5/7267
(Continued)

(56) References Cited

U.S. PATENT DOCUMENTS

2016/0120433 A1* 5/2016 Hughes ................ A61B 5/0205
600/483
2017/0360377 A1* 12/2017 Rossi ..................... A61B 5/364

FOREIGN PATENT DOCUMENTS

CN 201912077 U 8/2011
CN 102028459 B 1/2013
(Continued)

OTHER PUBLICATIONS

International Search Report for International Application No. PCT/CN2018/072349 dated Aug. 23, 2018, 2 pages.
(Continued)

*Primary Examiner* — Erin M Piateski
(74) *Attorney, Agent, or Firm* — TraskBritt

(57) ABSTRACT

An artificial intelligence-based interference recognition method for an electrocardiogram, comprising: cutting and sampling heart beat data of a first data amount, and inputting the heart beat data to be recognized that is obtained by cutting and sampling into an interference recognition binary classification model for interference recognition; in a sequence of the heart beat data, performing signal anomaly determination on a heart beat data segment where an inter-beat interval is greater than or equal to a preset interval determination threshold value, so as to determine whether the heart beat data segment is an abnormal signal; if the heart
(Continued)

beat data segment is not an abnormal signal, determining a starting data point and an ending data point of sliding sampling in the heart beat data segment according to a set time with a preset time width, and performing sliding sampling on the data segment from the starting data point until the ending data point so as to obtain multiple sampling data segments; and using each sampling data segment as heart beat data to be recognized for interference recognition.

8 Claims, 3 Drawing Sheets

(51) Int. Cl.
  *A61B 5/0456* (2006.01)
  *A61B 5/0472* (2006.01)
  *A61B 5/30* (2021.01)
  *A61B 5/352* (2021.01)
  *A61B 5/366* (2021.01)
(58) Field of Classification Search
  USPC .......................................................... 600/521
  See application file for complete search history.

(56) References Cited

FOREIGN PATENT DOCUMENTS

| | | |
|---|---|---|
| CN | 105380620 A | 3/2016 |
| CN | 104127194 B | 5/2016 |
| CN | 107358196 A | 11/2017 |
| CN | 106214123 B | 1/2019 |
| JP | 2017-525410 | 4/2018 |

OTHER PUBLICATIONS

International Written Opinion for International Application No. PCT/CN2018/072349 dated Aug. 23, 2018, 3 pages.
Japanese Office Action for Japanese Application No. 2020-591166 dated Dec. 16, 2020, 10 pages with machine translation.
Supplementary European Search Report and Opinion for European Application No. 18880831, dated Dec. 11, 2020, 6 pages.
Chinese Office Action for Chinese Application No. 201711203069 dated May 15, 2020, 11 pages.

* cited by examiner

ARTIFICIAL INTELLIGENCE-BASED INTERFERENCE RECOGNITION METHOD FOR ELECTROCARDIOGRAM

CROSS-REFERENCE TO RELATED APPLICATIONS

This application is a national phase entry under 35 U.S.C. § 371 of International Patent Application PCT/CN2018/072349, filed Jan. 12, 2018, designating the United States of America and published as International Patent Publication WO 2019/100561 A1 on May 31, 2019, and claims priority to Chinese Patent Application, filed to the Chinese Patent Office on Nov. 27, 2017, Application No. 201711203069.4, entitled "Artificial intelligence-based interference identification method for electrocardiogram."

TECHNICAL FIELD

The present disclosure relates to the technical field of artificial intelligence data analysis and processing, and more particularly, to an artificial intelligence-based interference identification method for electrocardiogram.

BACKGROUND

In 1908, Einthoven began to use electrocardiography (ECG) to monitor electrophysiological activities of a heart. At present, noninvasive ECG examination has become one of the important methods for diagnosis and screening heart diseases in clinical cardiovascular field. ECG examination can be divided into several categories such as resting ECG, ambulatory ECG and exercise ECG according to clinical application.

ECG monitoring is an important measure for observation, diagnosis and treatment of cardiovascular patients, and can monitor whether there is arrhythmia, a frequency of heart beat in real time, and thus, timely and effective measures can be taken according to ECG activities. Although most of ambulatory ECG analysis software in the market can automatically analyze data, in clinical work, ECG detection and recording process are susceptible to interference caused by various influences, resulting in invalid or inaccurate acquired data, which cannot correctly reflect condition of patients and increases difficulty and workload for doctors in diagnosis. Meanwhile, interference data is also a main factor that makes intelligent diagnostic tools unable to work effectively. Therefore, it is particularly important to minimize interference.

BRIEF SUMMARY

The purpose of the present disclosure is to provide an artificial intelligence-based interference identification method for electrocardiogram. An end-to-end two-classification identification system with deep learning algorithm as its core has characteristics of high precision and strong generalization performance, and it can effectively solve disturbance problems caused by main disturbance sources such as electrode falling off, motion interference and static interference, and thus, the problem of poor identification caused by various and irregular disturbance data in traditional algorithms is overcome.

To achieve the above purpose, the present disclosure provides an artificial intelligence-based interference identification method for electrocardiogram, including:

performing cutting and sampling on heart beat data with a first data amount, and inputting heart beat data to be identified obtained by the cutting and sampling into an interference identification two-classification model to identify interference;

determining a heart beat data segment with a heart beat interval greater than or equal to a preset interval determination threshold in a sequence of the heart beat data to be identified;

performing judgment of signal abnormality on the heart beat data segment with the heart beat interval greater than or equal to the preset interval determination threshold to determine whether the heart beat data segment is an abnormal signal;

if the heart beat data segment is not the abnormal signal, according to a set time value, determining a starting data point and an ending data point for sliding sampling in the heart beat data segment with a preset time width, and performing the sliding sampling on the data segment from the starting data point to the ending data point to obtain multiple sample data segments; and taking each of the sample data segments as the heart beat data to be identified and performing the interference identification method.

Preferably, the performing cutting and sampling on heart beat data with a first data amount specifically includes:

determining a sample midpoint of the heart beat data; and taking the sample midpoint as a center, according to a time sequence of the heart beat data, performing data interception from the sample midpoint to two ends to obtain the first data amount of sample data.

Further preferably, the sample midpoint of the heart beat data is a R point of QRS wave complex data in the heart beat data.

Further preferably, the data interception includes:

interception according to a number of data points or according to a length of a time period.

Preferably, the heart beat data is single-lead or multi-lead heart beat data, and the performing cutting and sampling on heart beat data with a first data amount includes:

determining a sample midpoint of the single-lead or multi-lead heart beat data; and performing the cutting and sampling based on the sample midpoint of the single-lead or multi-lead heart beat data with the first data amount.

Preferably, the inputting the heart beat data to be identified obtained by the cutting and sampling into an interference identification two-classification model to identify interference includes:

determining an interference noise probability value of the heart beat data to be identified of single-lead or multi-lead according to the interference identification two-classification model; and determining whether the heart beat data to be identified is interference data or non-interference data according to the interference noise probability value.

Further preferably, the method further includes: labeling the interference data.

Preferably, the method further includes: establishing the interference identification two-classification model based on artificial intelligence self-learning training.

Further preferably, the training includes:

labeling training data;

performing data format conversion and storage on the training data, and converting the data format into a preset standard data format; and performing training according to the training data in the preset standard data format.

The artificial intelligence-based interference identification method for electrocardiogram provided by the embodiments of the disclosure constructs an end-to-end two-classification identification system taking deep learning algorithm as a core, which has characteristics of high precision and strong generalization performance, and it can effectively solve disturbances generated by main disturbance sources such as electrode peeling off, motion interference and static interference. The method adopts an off-line trained deep learning model to classify input heart beat data, and a classification result of whether the heart beat data is interference or not is directly output. The result is obtained quickly, the identification accuracy is high, the stability performance is good, and effective and high-quality data can be provided for subsequent analysis.

DETAILED DESCRIPTION

Figure 1:
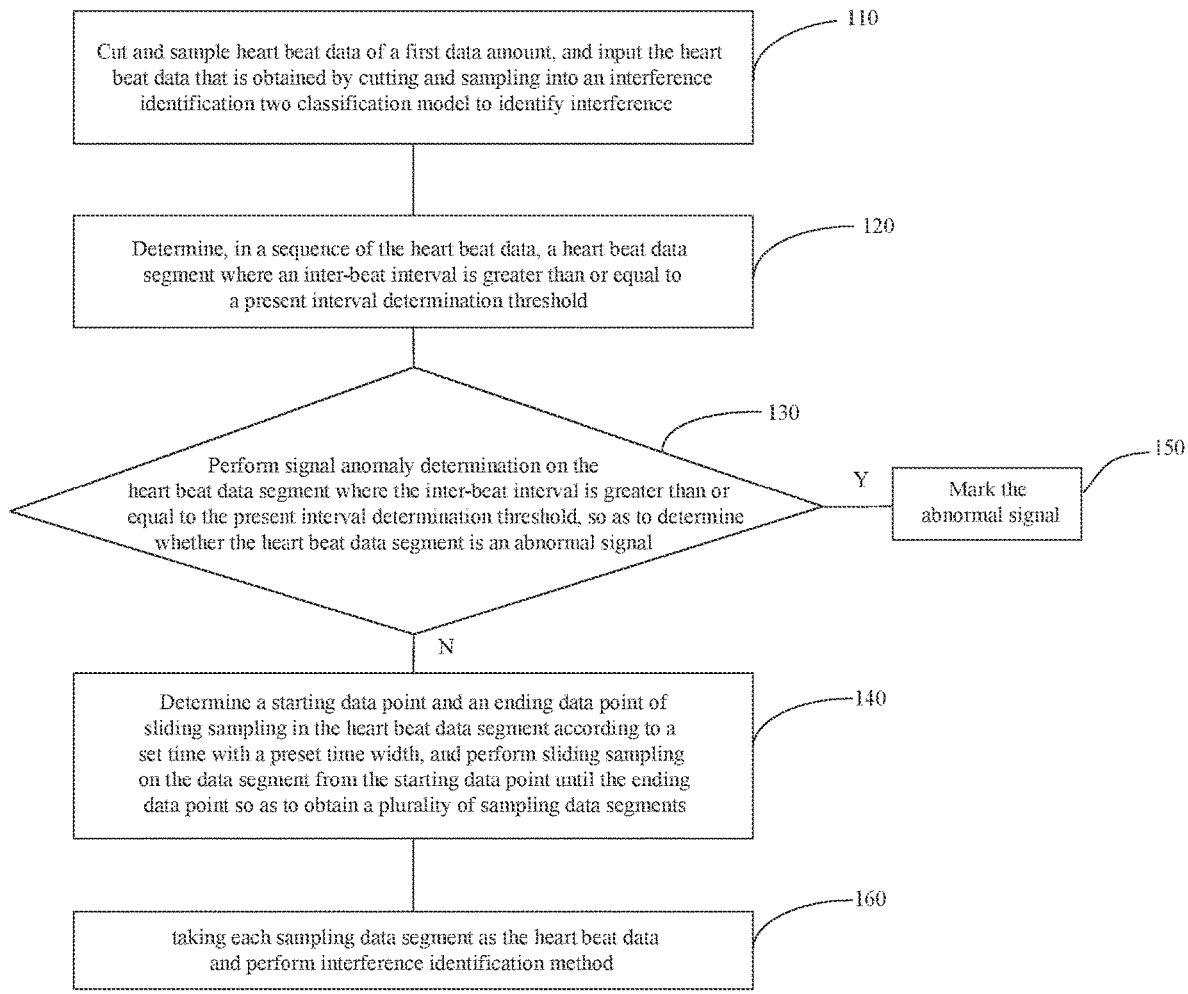
FIG. 1 is a flowchart illustrating an artificial intelligence-based interference identification method for electrocardiogram according to an embodiment of the present disclosure.

Technical solutions of the present disclosure will be further described in detail below through accompanying drawings and embodiments.

In order to facilitate understanding of the technical solutions of the present disclosure, basic principles of artificial intelligence models, especially convolutional neural network models, are first introduced.

Artificial intelligence Convolutional Neural Network (CNN) model is a supervised learning method in deep learning, which is a multi-layer network (hidden layer) connection structure that simulates a neural network. An input signal sequentially passes through each hidden layer, in which a series of complex mathematical processes (Convolution, Pooling, Regularization, prevention of over-fitting, Dropout, Activation, and general use of Rectified Linear Unit activation function) are carried out. Some features of an object to be identified are automatically abstracted layer by layer, these features are transmitted as input to a higher hidden layer for calculation until an entire signal is reconstructed by the last several full connection layers, and Softmax function is used to perform logistics regression to achieve multi-objective classification.

CNN belongs to the supervised learning method in artificial intelligence. In a training phase, the input signal is processed through multiple hidden layers to reach last full connection layers. There is an error between a classification result obtained by Softmax logical regression and a known classification result (label). One of core ideas of deep learning is to continuously minimize the error through a large number of sample iterations so as to calculate and obtain parameters for connecting neurons in each hidden layer. In this process, it is generally necessary to construct a special cost function, and quickly and effectively minimize all connection parameters in a neural network structure with complex depth (number of hidden layers) and breadth (dimension of features) by using a nonlinearly optimized gradient descent algorithm and an error back propagation (BP) algorithm.

In deep learning, data needed to be identified is input into a training model, and finally an identification result is output after the data passes through a first hidden layer, a second hidden layer and a third hidden layer. Features with different degrees of abstraction are extracted in each layer, and finally specific categories of original data are identified, such as cars, people or animals.

An algorithm model of deep learning is very complex in mathematics. Developing a complete algorithm program requires strong professional background knowledge and rich work experience. In recent years, companies such as GOOGLE®, Microsoft, Baidu, Facebook and some famous universities (such as University of California, Berkeley, and University of Montreal in Canada) have also successively developed and launched open source platforms for artificial intelligence development with different characteristics, helping some research and development companies in the field of deep learning to quickly master this cutting-edge technology. Among them, Caffe of Berkeley and Tensorflow of GOOGLE® are currently the two most widely used framework tools.

The model of deep learning is extremely complex, and training data needed is from hundreds of thousands, millions to tens of millions, coupled with repeated loop iterations, resulting in a very large amount of nonlinear optimized calculation. For an actual project, it often takes from a dozen hours to several days or even longer to calculate by using a central processing unit of a common computer. In this case, Graphics Processing Unit (GPU) replaces it to greatly speed up the calculation. At present, GPU cards provided by Nvidia company, due to powerful graphics and computer vision computing capabilities, a large number of computing database such as linear algebra, and supporting of parallel processing, can meet the computing of various methods with deep learning needs, and becomes a basic hardware for high-performance training and inference of current artificial intelligence.

The artificial intelligence-based interference identification method for electrocardiogram of the present disclosure is implemented based on the CNN model.

The flowchart of the artificial intelligence-based interference identification method for electrocardiogram shown in FIG. 1 below illustrates specific implementation of the technical solutions of the present disclosure.

As shown in FIG. 1, the artificial intelligence-based interference identification method for electrocardiogram provided by the present disclosure includes as follows.

Figure 3:
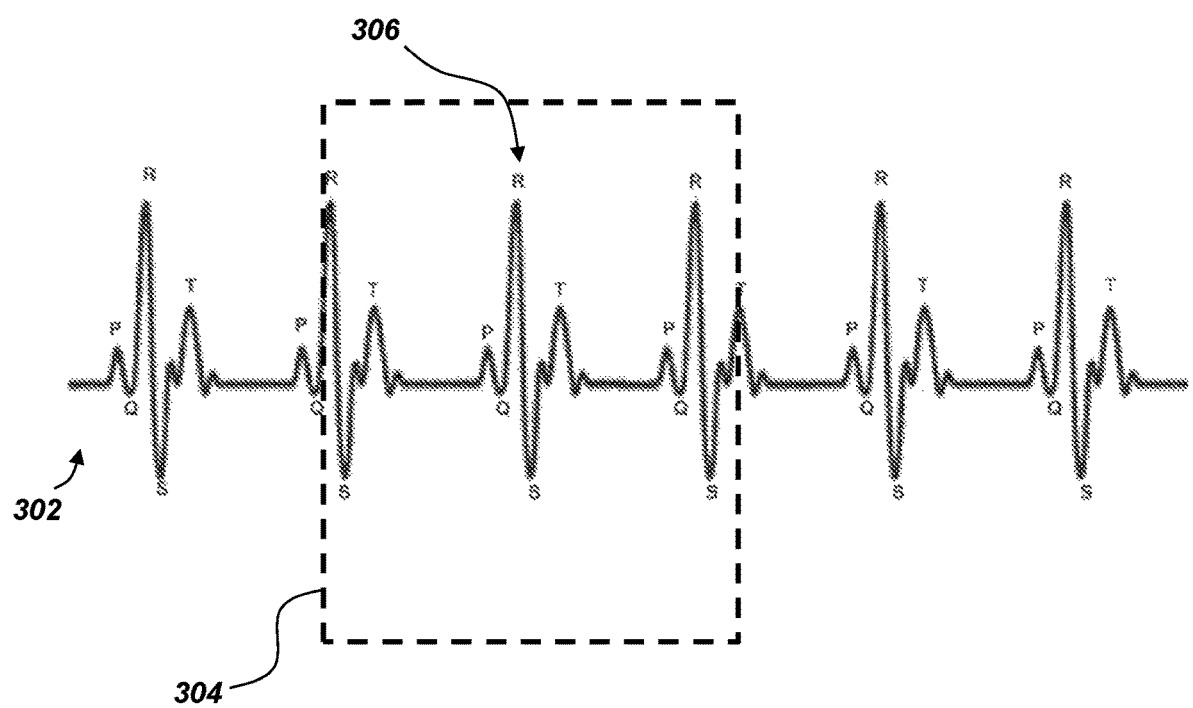
FIG. 3 is a graphical representation of a QRS wave complex during the artificial intelligence-based interference identification method of FIG. 1.

Step 110, further illustrated in FIG. 3, cutting and sampling are performed on heart beat data 302 with a first data amount, and heart beat data to be identified obtained by cutting and sampling is input into an interference identification two-classification model to identify interference.

Firstly, a sample midpoint 306 of the heart beat data 302 is determined, and specifically, a R point of QRS wave complex data in the heart beat data may be selected. Then, taking the sample midpoint 306 as a center, according to a time sequence of the heart beat data, data interception is performed from the sample midpoint 306 to two ends, and the first data amount of sample data 304 is obtained. Data interception may be performed according to a number of data points or according to a length of a time period.

The above cutting and sampling may be for single-lead or multi-lead. In the case of multi-lead, the sample midpoint 306 of the heart beat data 302 of each lead can be determined separately for each lead, and then cutting and sampling are performed based on the sample midpoint 306 of the heart beat data 302 of each lead with the first data amount. In other words, a same amount of data is intercepted forward and backward from the sample midpoint 306. Interception can be specifically carried out according to a set number of the data points or according to a set length of the time period.

In the present disclosure, the specific implementation solution of that to identify interference may be to determine an interference noise probability value of the heart beat data to be identified for each lead according to the interference identification two-classification model, and then determine whether the heart beat data to be identified is interference data or non-interference data according to the interference noise probability value.

Training of the interference identification two-classification model will be described in detail in the following.

Step 120, a heartbeat data segment with a heartbeat interval greater than or equal to a preset interval determination threshold in the sequence of the heart beat data to be identified is determined.

Specifically, the preset interval may preferably be 2 seconds. If the heart beat interval is greater than or equal to the preset interval, it indicates that there may be signal abnormality, so it is necessary to perform a judgment of signal abnormality first.

Step 130, the judgment of signal abnormality is performed on the heart beat data segment with the heart beat interval greater than or equal to the preset interval determination threshold to determine whether the heart beat data segment is an abnormal signal.

Specifically, the judgment of signal abnormality includes the judgment of signal overflow, low voltage, electrode peeling off, etc. For the heart beat data with the heart beat interval greater than or equal to 2 seconds, whether it is signal overflow, low voltage or electrode peeling off is first judged with the interference identification two-classification model.

If it is not an abnormal signal, step 140 is executed. If it is an abnormal signal, step 150 is executed.

Step 140, according to a set time value, a starting data point and an ending data point for sliding sampling in the heart beat data segment are determined with a preset time width, and sliding sampling is performed on the data segment from the starting data point to the ending data point to obtain multiple sample data segments.

In other words, according to the set time value, the starting data point of a first sample data segment of the heart beat data in the foremost of time sequence is determined, and then non-overlapped sliding sampling with the preset time width is performed backward continuously according to the present time width. Preferably, the number of data points included in each sample data segment is also the first data amount.

Then, step 160 is executed.

Step 150, the abnormal signal is labeled, returns to step 120, and next heart beat data segment with heart beat interval greater than or equal to the preset interval determination threshold continues to be identified.

Step 160, each of the sample data segments is taken as the heart beat data to be identified and the interference identification method is performed.

Further, the interference data that is identified is labeled.

The above-mentioned structure of the interference identification two-classification model is an end-to-end two-classification identification system inspired and constructed by artificial intelligence deep learning CNN models such as LeNet-5 and AlexNet.

For the training of the model, nearly 4 million accurately labeled data segments from 300,000 patients are used. Labeling is divided into two categories: normal ECG signals or ECG signal fragments with obvious interference. The segments are labeled by custom-developed tools, and then interference fragment information is saved in a customized standard data format.

In the training process, two GPU servers are used for dozens of round-robin training. In a specific example, for a segment D [300] with a sample rate of 200 Hz and a data length of 300 ECG voltage values (millivolts), input data is: InputData (i, j), wherein i is a i-th lead, and j is a j-th segment of the i-th lead. All input data is randomly scattered before training, which ensures convergence of the training process. At the same time, collection of too many samples from the ECG data of a same patient is controlled, improving the generalization ability of the model, that is, an accuracy rate in a real scene. After the training converges, one million pieces of independent test data are used for testing, and the accuracy rate can reach 99.3%. Additionally, specific test data is shown in Table 1 below.

TABLE 1

|  | Interference | Normal |
| --- | --- | --- |
| Sensitivity | 99.14% | 99.32% |
| Positive Predictivity | 96.44% | 99.84% |

Interference data is often caused by external disturbance factors, mainly including electrode peeling off, low voltage, electrostatic interference and motion interference. Not only interference data generated by different disturbance sources is different, but also interference data generated by a same disturbance source is diverse. At the same time, considering that although the diversity of interference data is widely distributed, the difference with normal data is very large, so the diversity is ensured as much as possible when collecting interference training data. Furthermore, moving window sliding sampling is adopted to increase the diversity of interference data as much as possible, so as to make the model robust to interference data. Even if interference data in the future is different from any previous interference, with comparison to normal data, its similarity with interference is greater than normal data, thus enhancing the ability of the model to identify interference data.

Figure 2:
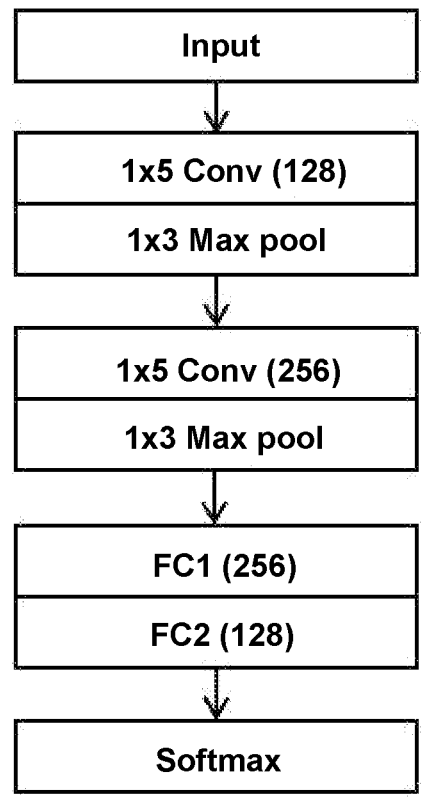
FIG. 2 is a schematic diagram illustrating an interference identification two-classification model according to an embodiment of the present disclosure.

The interference identification two-classification model adopted in this step can be shown in FIG. 2. The network first uses two convolutional layers, the convolution kernel in size is 1×5, and each layer is followed by a maximum pooling. The number of the convolution kernel starts from 128, and the number of the convolution kernel doubles every time passing a maximum pooling layer. The convolutional layers are followed by two full connection layers and a Softmax classifier. Since the classification number of the model is two, Softmax has two output units that correspond to corresponding categories in turn, and uses cross entropy as the cost function.

The artificial intelligence-based interference identification method for electrocardiogram provided by the embodiments of the disclosure constructs an end-to-end two-classification identification system taking deep learning algorithm as a core, which has characteristics of high precision and strong generalization performance, and can effectively solve disturbances generated by main disturbance sources such as electrode peeling off, motion interference and static interference. The method adopts an off-line trained deep learning model to classify input heart beat data, and a classification result of whether the heart beat data is interference or not is directly output. The result is obtained quickly, the identification accuracy is high, the stability performance is good, and effective and high-quality data can be provided for subsequent analysis.

Those skilled in the art should further realize that the units and algorithm steps of the examples described in the embodiments disclosed herein can be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. An artificial intelligence-based interference identification method for electrocardiogram, comprising:
   performing cutting and sampling on heart beat data with a first data amount, and inputting heart beat data obtained by the cutting and sampling into an interference identification two-classification model to identify interference;
   determining a heart beat data segment with a heart beat interval greater than or equal to a preset interval determination threshold in a sequence of the result of the cutting and sampling on heart beat data;
   performing judgment of signal abnormality on the heart beat data segment with the heart beat interval greater than or equal to the preset interval determination threshold to determine whether the heart beat data segment is an abnormal signal;
   if the heart beat data segment is the abnormal signal, labeling it, and continue determining the next heart beat data segment with a heart beat interval greater than or equal to a preset interval determination threshold in a sequence of the result of the cutting and sampling on heart beat data;
   if the heart beat data segment is not the abnormal signal, according to a set time value, determining a starting data point and an ending data point for sliding sampling in the heart beat data segment with a preset time width, and performing the sliding sampling on the data segment from the starting data point to the ending data point to obtain multiple sample data segments; and
   taking each of the sample data segments of the heart beat data into an interference identification two-classification model to identify interference, and performing the interference identification method;
   wherein the performing cutting and sampling on heart beat data with the first data amount comprises:
      determining an interference noise probability value of the heart beat data of single-lead or multi-lead according to the interference identification two-classification model; and
      determining whether the heart beat data is interference data or non-interference data according to the interference noise probability value.

2. The method according to claim 1, wherein the performing cutting and sampling on heart beat data with a first data amount comprises:
   determining a sample midpoint of the heart beat data; and
   taking the sample midpoint as a center, according to a time sequence of the heart beat data, performing data interception from the sample midpoint to two ends to obtain the first data amount of sample data.

3. The method according to claim 2, wherein the sample midpoint of the heart beat data is a R point of QRS wave complex data in the heart beat data.

4. The method according to claim 2, wherein the data interception comprises:
   interception according to a number of data points or according to a length of a time period.

5. The method according to claim 1, wherein the heart beat data is single-lead or multi-lead heart beat data, and the performing cutting and sampling on heart beat data with a first data amount comprises:
   determining a sample midpoint of the single-lead or multi-lead heart beat data; and
   performing the cutting and sampling based on the sample midpoint of the single-lead or multi-lead heart beat data with the first data amount.

6. The method according to claim 1, further comprising: labeling the interference data.

7. The method according to claim 1, further comprising: establishing the interference identification two-classification model based on artificial intelligence self-learning training.

8. The method according to claim 7, wherein the training comprises:
   labeling training data;
   performing data format conversion and storage on the training data, and converting the data format into a preset standard data format; and
   performing training according to the training data in the preset standard data format.

* * * * *